(12) United States Patent
Ramos et al.

(10) Patent No.: US 10,222,312 B2
(45) Date of Patent: Mar. 5, 2019

(54) CRYOGENIC TEMPERATURE CONTROLLER FOR VOLUMETRIC SORPTION ANALYZERS

(71) Applicants: Enrique Gadea Ramos, Boynton Beach, FL (US); Sean C. Lacov, Boynton Beach, FL (US); Brandegee C. Pierce, Boynton Beach, FL (US); Armando H. Solar-Schultz, Boynton Beach, FL (US); Matthias Thommes, Boynton Beach, FL (US); Karl M. Wahlfrid, Boynton Beach, FL (US); Albert J. Woodcock, Boynton Beach, FL (US)

(72) Inventors: Enrique Gadea Ramos, Boynton Beach, FL (US); Sean C. Lacov, Boynton Beach, FL (US); Brandegee C. Pierce, Boynton Beach, FL (US); Armando H. Solar-Schultz, Boynton Beach, FL (US); Matthias Thommes, Boynton Beach, FL (US); Karl M. Wahlfrid, Boynton Beach, FL (US); Albert J. Woodcock, Boynton Beach, FL (US)

(73) Assignee: Anton Paar Quantatec, Inc., Boynton Beach, FL (US)

( * ) Notice: Subject to any disclaimer, the term of this patent is extended or adjusted under 35 U.S.C. 154(b) by 142 days.

(21) Appl. No.: 15/624,042

(22) Filed: Jun. 15, 2017

(65) Prior Publication Data

US 2017/0370817 A1 Dec. 28, 2017

Related U.S. Application Data

(60) Provisional application No. 62/355,449, filed on Jun. 28, 2016.

(51) Int. Cl.
*G01N 15/08* (2006.01)
*G01N 1/42* (2006.01)

(52) U.S. Cl.
CPC ........... *G01N 15/0806* (2013.01); *G01N 1/42* (2013.01); *G01N 15/0893* (2013.01)

(58) Field of Classification Search
CPC ... G01N 1/42; G01N 15/0806; G01N 15/0893
See application file for complete search history.

(56) References Cited

U.S. PATENT DOCUMENTS 3,176,472 A * 4/1965 Cox .................... A61B 10/0096
                                                           62/3.6
3,236,133 A * 2/1966 De Pas .................... F25D 17/00
                                                           62/331

(Continued)

FOREIGN PATENT DOCUMENTS

WO      WO-0045956 A1 *  8/2000  .............. B01D 1/30

OTHER PUBLICATIONS

Matthias Thommes, et al., Physisorption of Gases, With Special Reference to the Evaluation of Surface Area and Pore Size Distribution (IUPAC Technical Report), Pure Appl. Chem. 2015; 87(9-10): 1051-1069, De Gruyter, Research Triangle Park, North Carolina, USA.

*Primary Examiner* — David J Bolduc
(74) *Attorney, Agent, or Firm* — Robert M. Schwartz; Alfred K. Dassler

(57) ABSTRACT

A cryogenic temperature controller assembly includes a controller and a thermostatic block that has a chamber for receiving a sample holder therein. The thermostatic block has a heat sink with an exposed surface for exposure to a cryogenic fluid. A heater is disposed intermediate the exposed surface and the chamber. The heater is connected to the controller. A temperature probe is disposed in the thermostatic block. The probe is connected to the controller. The (Continued)

controller regulates the heater based on an actual temperature from the probe to maintain a predetermined set point temperature in the thermostatic block.

19 Claims, 5 Drawing Sheets

(56) References Cited

U.S. PATENT DOCUMENTS

| | | | |
|---|---|---|---|
| 3,836,779 A | 9/1974 | Bruno et al. | |
| 4,672,202 A * | 6/1987 | Crossley, Jr. | G01J 5/061 250/238 |
| 4,712,607 A * | 12/1987 | Lindemans | A01N 1/02 165/263 |
| 4,888,956 A * | 12/1989 | le Roux Murray | F25C 1/00 62/51.1 |
| 4,984,628 A * | 1/1991 | Uchida | B01L 7/02 165/256 |
| 5,181,382 A * | 1/1993 | Middlebrook | G02B 21/28 219/201 |
| 5,239,482 A * | 8/1993 | Ajot | G01N 15/0893 702/30 |
| 5,305,825 A | 4/1994 | Roehrich et al. | |
| 5,408,864 A * | 4/1995 | Wenman | G01N 15/08 73/38 |
| 5,598,888 A * | 2/1997 | Sullivan | G01N 1/42 165/263 |
| 5,613,366 A | 3/1997 | Schoenman | |
| 5,646,335 A * | 7/1997 | Wenman | G01N 15/08 73/38 |
| 5,829,256 A * | 11/1998 | Rada | A61B 10/0096 62/51.1 |
| 6,094,923 A * | 8/2000 | Rada | A61B 10/0096 62/381 |
| 6,387,704 B1 * | 5/2002 | Thomas | G01N 15/0893 436/43 |
| 6,413,252 B1 * | 7/2002 | Zavislan | A61B 18/02 359/375 |
| 6,595,036 B1 * | 7/2003 | Nakai | G01N 15/0893 422/69 |
| 7,043,968 B1 * | 5/2006 | Hildebrandt | G01N 11/14 73/54.28 |
| 7,320,224 B2 * | 1/2008 | Ash | F04B 37/08 62/55.5 |
| 8,596,340 B1 * | 12/2013 | Horn, Jr. | B01L 99/00 165/104.11 |
| 8,826,728 B1 * | 9/2014 | Hildebrandt | G01N 33/2888 73/54.43 |
| 2006/0057555 A1 * | 3/2006 | Damari | A01N 1/02 435/4 |
| 2006/0236703 A1 * | 10/2006 | Rada | A01N 1/02 62/62 |
| 2007/0261429 A1 * | 11/2007 | Teehan | A01N 1/02 62/378 |
| 2011/0229928 A1 * | 9/2011 | Dorward | G01N 1/42 435/29 |
| 2012/0292528 A1 * | 11/2012 | Oh | G01N 3/42 250/443.1 |
| 2013/0125673 A1 * | 5/2013 | Kanipayor | B01L 3/04 73/863.11 |
| 2014/0335614 A1 * | 11/2014 | Schryver | A01N 1/0263 435/374 |
| 2015/0346069 A1 * | 12/2015 | Inoue | G01N 1/42 73/863.11 |
| 2015/0355061 A1 * | 12/2015 | Inoue | G01N 1/42 73/863.11 |
| 2016/0223463 A1 * | 8/2016 | Schmidt | G01N 21/65 |

* cited by examiner

CRYOGENIC TEMPERATURE CONTROLLER FOR VOLUMETRIC SORPTION ANALYZERS

CROSS REFERENCE TO RELATED APPLICATIONS

This application claims benefit of U.S. Provisional Patent Application No. 62/355,449 filed Jun. 28, 2016, titled Cryogenic Temperature Controller And Its Use In Volumetric Sorption Analyzers, the disclosure of which is incorporated herein by reference in its entirety.

BACKGROUND OF THE INVENTION

Field of the Invention

The invention relates to a device for heating and regulating an intermediate thermal conductor to allow the scientist to conduct physical adsorption experiments with an adsorption medium utilizing liquid Nitrogen as the primary coolant.

Description of the Related Art

Characterization of surface area and porosity of materials is widely performed by Nitrogen adsorption at the temperature of the boiling point of liquid Nitrogen (77K) using different well established existing techniques (mainly gravimetric and volumetric methods).

However, a recent IUPAC study, published by De Gruyter, which is readily available for review with the use of any web search engine by searching the phrase "PAC-2014-1117", states that the technique of using Nitrogen has some weaknesses for the micropore distribution determination of samples. These weaknesses can be overcome by using Argon instead of Nitrogen as an analysis gas. For such instances, the analysis must be performed at the temperature of the boiling point of Argon (87K).

Accordingly, to use Argon as the analysis gas, existing analyzers primarily use three different techniques for controlling samples at the Argon boiling point temperature (which is greater than the boiling point of liquid Nitrogen), each of which have some disadvantages. 1) Immersion in liquid Argon: availability of liquid Argon is not widespread as liquid Nitrogen and the cost of liquid Argon is much higher than liquid Nitrogen; 2) controlling the temperature of the Argon with a cryostat: the amount of time a cryostat can maintain the target temperature is often not enough for completing an analysis and the cost of cryostats are high; and 3) controlling the temperature with a compression cryocooler: the cost of these systems are very high.

SUMMARY OF THE INVENTION

It is accordingly an object of the invention to provide a method and device for controlling temperature of an analysis gas, which overcomes the above-mentioned and other disadvantages of the heretofore-known devices and methods of this general type and which provides for an improvement over the prior art and solves both the problem of accurate temperature control while significantly reducing cost of using Argon (or any other costlier gases) as the analysis gas. The present invention controls sub-ambient temperatures to be used with volumetric sorption analyzers that makes use of liquid Nitrogen, similar cryogenic fluids (any fluid with a boiling point less than 123.15K) or sub-ambient fluids (liquids at temperatures less than 220K) as cooling fluid, allowing for flexibility in analysis duration and cost by controlling the temperature locally at a sample.

The present invention provides an apparatus that permits sorption analysis at temperatures greater than, or equal to, the temperature of a given cryogenic fluid. This is achieved by a thermostatic block made with a material having a high thermal conductivity (thermal conductivity greater than 35 W/m*K) surrounded by a thermal insulation material (preferably an insulation foam or a vacuum chamber or a combination of both with a thermal conductivity less than 1.1 W/m*K) and with a heat sink made with a material having a high thermal conductivity (thermal conductivity greater than 35 W/m*K). The heat sink is, in turn, partially immersed in a cooling fluid (preferably liquid Nitrogen) and is surrounded by a thermal insulation material (preferably an insulation foam or a vacuum chamber or a combination of both with a thermal conductivity less than 1.1 W/m*K) with the exception of a portion which is in direct contact with the cooling fluid. A heater is provided in the apparatus and is positioned between the thermostatic block and the portion of the heat sink in contact with the cooling fluid.

One part of a sample holder (where the sample to be analyzed) is placed inside the thermostatic block while the other part is connected to a volumetric analyzer.

The temperature of the thermostatic block is established by the equilibrium between the cooling capacity of the heat sink, the power introduced by the heater and the heat losses through the insulation. The cooling capacity of the heat sink changes very little with any fill level change (due to evaporation) of the cryogenic fluid since the major part of the heat transfer is performed by the part of the heat sink directly exposed to the cryogenic fluid, where the part of the heat sink directly exposed to the cryogenic fluid is well below the fill level of the vessel. The insulation material is impermeable to the cryogenic fluid. The insulation material and the dimensions thereof are selected so the total heat transfer through the surface of the material is smaller than the total heat transfer of the heat sink.

A temperature probe is installed in the thermostatic block and temperature readings from the temperature probe are processed by a temperature controller that regulates the heater output in order to achieve a pre-established target temperature in the thermostatic block (at the temperature probe).

The system of the present invention can maintain the target temperature in the thermostatic block for a long period of time (dependent on specific configuration) as shown in FIG. 4. Moreover, the analysis duration using the system can be extended indefinitely if the cryogenic fluid is refilled either manually or automatically. This is because the refilling process has an insignificant effect on the thermostatic block temperature stability.

With the foregoing and other objects in view there is provided, a cryogenic temperature controller assembly that includes a controller and a thermostatic block that has a chamber for receiving a sample holder therein. The thermostatic block has a heat sink with an exposed surface for exposure to a cryogenic fluid. A heater is disposed intermediate the exposed surface and the chamber. The heater is connected to the controller. A temperature probe is disposed in the thermostatic block. The probe is connected to the controller. The controller regulates the heater based on an actual temperature from the probe to maintain a predetermined set point temperature in the thermostatic block In accordance with another feature of the invention, an insulation sleeve at least partially surrounds the thermostatic block.

In accordance with an added feature of the invention, the insulation sleeve includes a portion surrounding the heat sink.

In accordance with an additional feature of the invention, an insulation cap mates with the insulation sleeve and covers an end of the thermostatic block.

In accordance with yet an additional feature of the invention, the heat sink is a rod that is thermally conductively connected to the thermostatic block and extends therefrom.

In accordance with yet another added feature of the invention, the heater is disposed at a juncture between the rod and the thermostatic block.

In accordance with still another added feature of the invention, a threaded connection is between the thermostatic block and the rod.

In accordance with yet still another added feature of the invention, the threaded connection includes a female tap hole with a base, the heater is disposed in the tap hole at the base.

In accordance with yet still another further feature of the invention, a vessel has a basin for receiving the thermostatic block and the heat sink and the cryogenic fluid.

In accordance with still a further feature of the invention, the heat sink is a rod that is thermally conductively connected at a connection to the thermostatic block, the rod extends to a position next to a base of the basin to allow the exposed surface to maintain contact with the cryogenic fluid at a low level of fill of the basin.

In accordance with still another feature of the invention, the rod has a free end opposite of the connection, the free end having an end cap for preventing the rod from damaging the basin.

In accordance with yet an additional feature of the invention, a sample holder is at least partially disposed in the chamber.

In accordance with yet an added feature of the invention, an insulation sleeve at least partially surrounds the thermostatic block and a portion at least partially surrounds the heat sink.

In accordance with yet a further feature of the invention, an insulation cap covers an end of the thermostatic block.

In accordance with yet a further feature of the invention, the thermostatic block has two chambers for simultaneously carrying out two separate sample analyses.

With the objects of the invention in view, there is also provided a cryogenic temperature controller assembly that includes a thermostatic block with a chamber for receiving a sample holder therein. The thermostatic block has a heat sink with an exposed surface for exposure to a cryogenic fluid. A temperature probe is disposed in the thermostatic block. A heater is disposed and configured for maintaining a predetermined set point temperature in the thermostatic block by introducing thermal energy on the basis of actual temperatures observed by the temperature probe.

In accordance with still a further feature of the invention, an insulation sleeve partially surrounding said thermostatic block.

In accordance with still another feature of the invention, a controller connected to said heater and said temperature probe, said controller regulating said heater based on actual temperatures observed by said probe for maintaining the predetermined set point temperature in said thermostatic block.

With the foregoing and other objects in view there is also provided a method for maintaining a predetermined set point temperature during a testing period. The method provides a thermostatic block that has a heat sink with an exposed surface. The exposed surface of the heat sink is brought into contact with a cryogenic fluid during the testing period to cool the thermostatic block. The method regulates a heater disposed to maintain the predetermined set point temperature in the thermostatic block by introducing thermal energy into the thermostatic block on the basis of actual temperatures observed by the temperature probe to maintain the predetermined set point temperature in the thermostatic block during the testing period.

Although the invention is illustrated and described herein as embodied cryogenic temperature controller for volumetric sorption analyzers, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
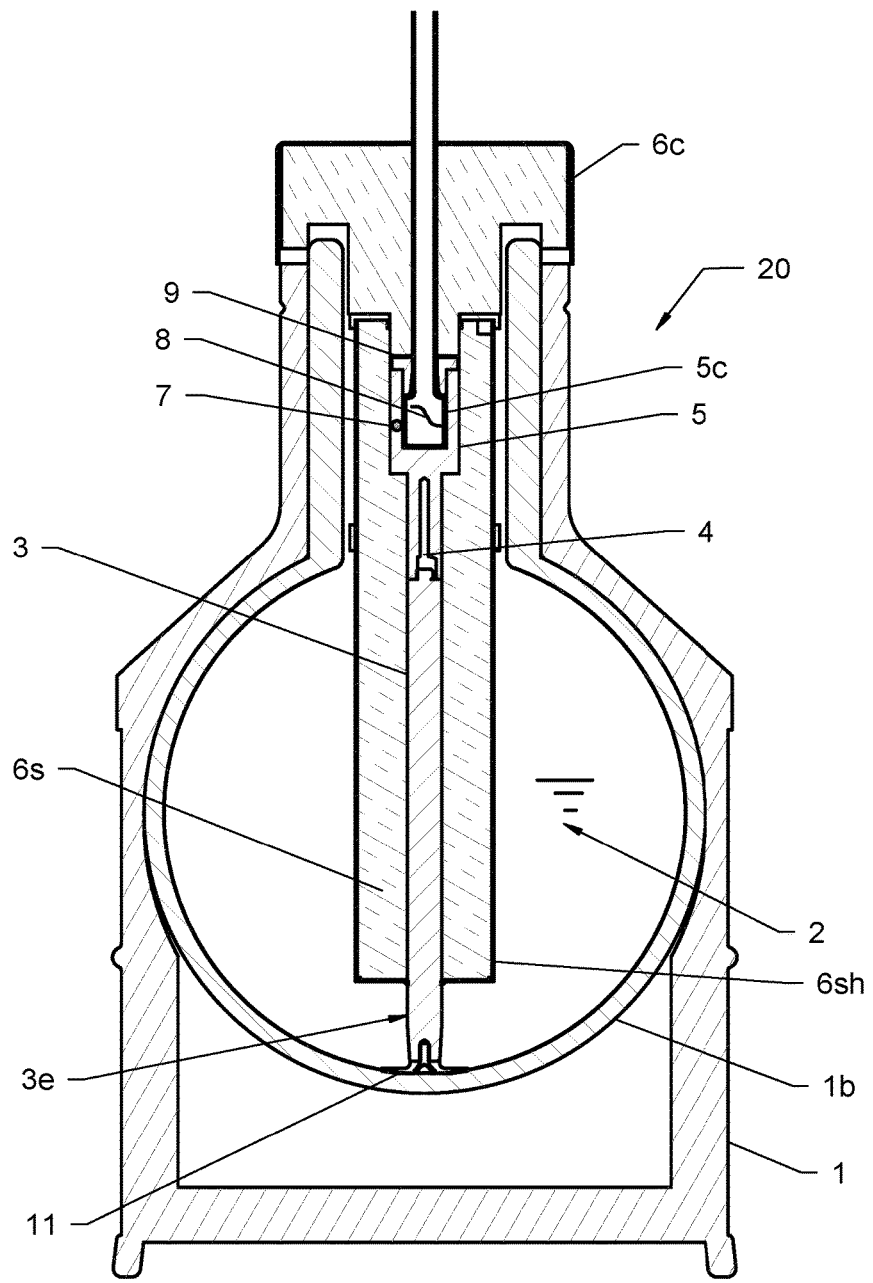
FIG. 1 is section view of an assembly including a cryogenic temperature control device.

Referring now to the drawing figures in which like reference designators refer to like elements, there is shown in FIG. 1, a temperature control device for sorption analyzation assembly 20. The assembly 20 includes a vessel 1 that may be provided as a vacuum flask that includes a fluid filing basin 1b that is filled with a cryogenic fluid 2 such as liquid Nitrogen, which is readily available.

Figure 2:
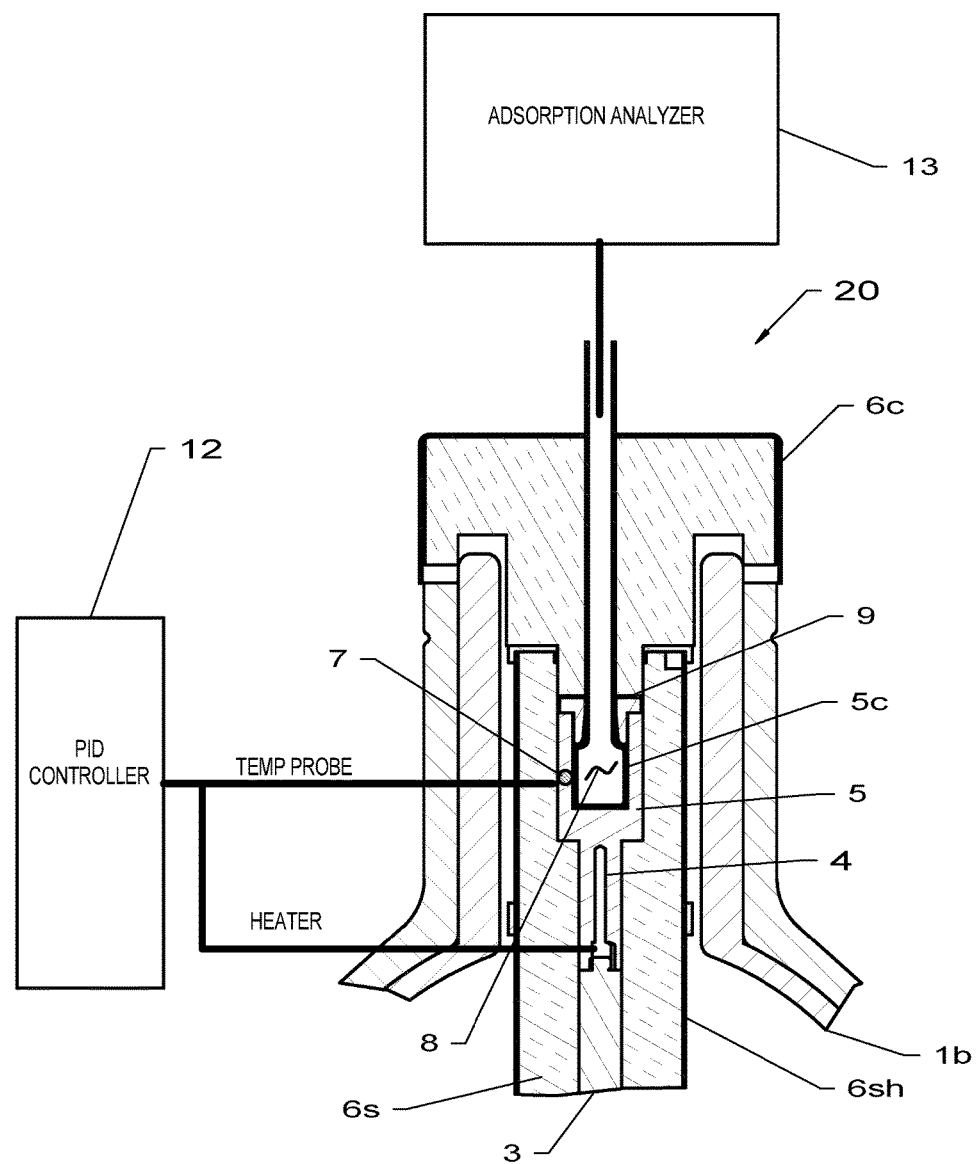
FIG. 2 is an enlarged section view along a different cutting plane than FIG. 1.

A thermostatic block 5 includes a chamber 5c, which receives a sample holder 8 therein. The chamber 5c is dimensioned to correspond to the outside diameter of the sample holder 8, so that the sample holder 8 is in heat conducting contact with the wall defining the chamber 5c. The sample holder 8 holds the sample that is to be tested and an analysis gas such as argon. The sample holder 8 is connected to a volumetric sample/adsorption analyzer 13, shown in FIG. 2. A lid 9 can be made of copper and defines an axial end wall of the chamber 5c. The lid 9 has an outside diameter that fits into the chamber 5c and a shoulder which rests on an end surface of the thermostatic block 5. The lid 9 has an aperture that is a pass through for the sample holder 8. The lid 9 closes the chamber 5c. The insulation material cap 6c has a male feature that is inserted into a female feature in the insulation material sleeve 6s surrounding the thermostatic block 5. The fit between the insulation material cap 6c and the insulation material sleeve 6s is a line to line fit. When the insulation material cap 6c is in place, a shoulder of the insulation material cap 6c can seat against a rim of the vacuum flask 1 to prevent Nitrogen in the basin 1b from evaporating. The thermostatic block 5 may be cylindrical and is made of a highly thermally conductive material (greater than 35 W/m*K), preferably a copper block of approximately 1.0 inch OD, 0.5 inches ID and 2 inches in height.

The thermostatic block 5 has a heat sink portion 3 that is in thermal conducting contact therewith. In FIG. 1, the heat sink portion 3 is shown as a cylindrical rod 3 that is rigidly affixed to the thermostatic block 5 and which coaxially extends from the thermostatic block 5 into the basin 1b. The rod 3 may be affixed onto the thermostatic block 5 by a threaded connection (male threaded portion and female threaded portion). In a preferred configuration, the heat sink rod 3 is aluminum, and is a cylindrical rod approximately 8 inches in length with a cross sectional diameter of 0.3-0.5 inches.

The rod 3 is partially surrounded by the insulation material sleeve 6s that also surrounds a longitudinal extent of the thermostatic block 5. The rod 3 is free of insulation material at an exposed surface 3e that is in thermal contact with the cryogenic fluid 2 (opposite the thermostatic block 5 at a base of the basin 1b). The insulation material for the insulation sleeve 6s and the insulation cap 6c may be a dense, closed cell foam (preferably polyisocyanurate) barrier of 0.5-1.0 inch thickness. Furthermore, a cylindrical outer surface of the insulation material sleeve 6s may be provided with a sheath 6sh to protect the insulation material sleeve 6s from wear during handling of the assembly 20. The sheath 6sh can be made of steel. It is also possible for either or both of the insulation cap 6c and the insulation sleeve 6s to be encased in a liner and internally vacuumed by connection to a vacuum pumping system, which provides for a reduced thermal conductivity and thus a better insulation. Alternatively, the liner is vacuumed and sealed during manufacture of the particular insulation material component, to maintain the vacuum. The exposed surface 3e that is not covered by the insulation material sleeve 6s is opposite the location of the thermostatic block 5. The insulation material cap 6c and the insulation sleeve 6s are releasably connected to one another for removing the sample holder 8 and or for refilling cryogenic fluid 2 into the basin 1b. A distal end (end of the exposed surface) of the rod 3 may be provided with a soft material tip 11, such as plastic to prevent damage to the glass of the basin 1b, when inserting the device into the vacuum flask 1.

The apparatus 20 includes at least one heater 4 in a position that is intermediate the exposed surface 3e of the heat sink 3 and the chamber 5c. As an example, heater 4 may be installed in the heat sink 3 at a location not in direct contact with the cryogenic fluid 2 i.e. along a portion of the heat sink 3 underneath the insulation material sleeve 6s. Such position allows the heater 4 to control the energy removed from the thermostatic block 5 by the cryogenic fluid 2 via the heat sink 3. A particular suitable position for the heater 4, is recessed at a juncture between the thermal block 5 and the heat sink rod 3. In the FIGS. 1 and 2, the heater 4 is provided in a base of a blind hole formed in the thermostatic block 5 that includes female threads which are threaded to male threads on the heat sink rod 3. The heater 4 may be a resistance heater (cartridge, rod, ring, or band heater) or alternatively the heater 4 may be a susceptor that is heated by an induction coil. The heater 4 can be provided with conductive grease or paste to maximize the conduction from the heater 4 to the corresponding thermally conductive material. The heater provides energy between the thermostatic block 5 and the cryogenic fluid 2 to limit the amount of heat removed by the cryogenic fluid 2.

The thermostatic block 5 includes a temperature probe/thermal detection device 7, which is a PT100 (Platinum Resistance Temperature Detector) that is utilized in conjunction with a PID (proportional-integral-derivative) controller 12 or similar thermal control device (shown in FIG. 2.) to regulate the heater 4 and control and maintain the temperature within the thermostatic block 5 (thus at the chamber 5c) for the purpose of thermal control of the sample holder 8 and the contents disposed therein. In this regard, temperatures from the temperature probe 7 are processed by the temperature controller 12 that regulates the heater output in order to achieve and precisely maintain a pre-established set point temperature.

The temperature of the thermostatic block 5 is established by the equilibrium between the cooling capacity of the heat sink 3, the power introduced by the heater 4, and the heat losses through the insulation material 6. The cooling capacity of the heat sink 3 changes very little with the level change (due to evaporation) of the cryogenic fluid 2 since the major part of the heat transfer is carried out by the exposed surface 3e that is in contact with the cryogenic fluid 2. The insulation material 6 is not permeable to the cryogenic fluid 2. The insulation material 6 is dimensioned so the total heat transfer therethrough is less than the total heat transfer of the heat sink 3.

For more localized temperature control, it is possible to provide the thermostatic block 5 with multiple heat sinks 3, where each of the heat sinks 3 is provided with a respective heater and a respective thermal detection device 7. In this case, the controller 12 would control the respective heaters 4 individually based upon the corresponding temperatures.

Figure 4:
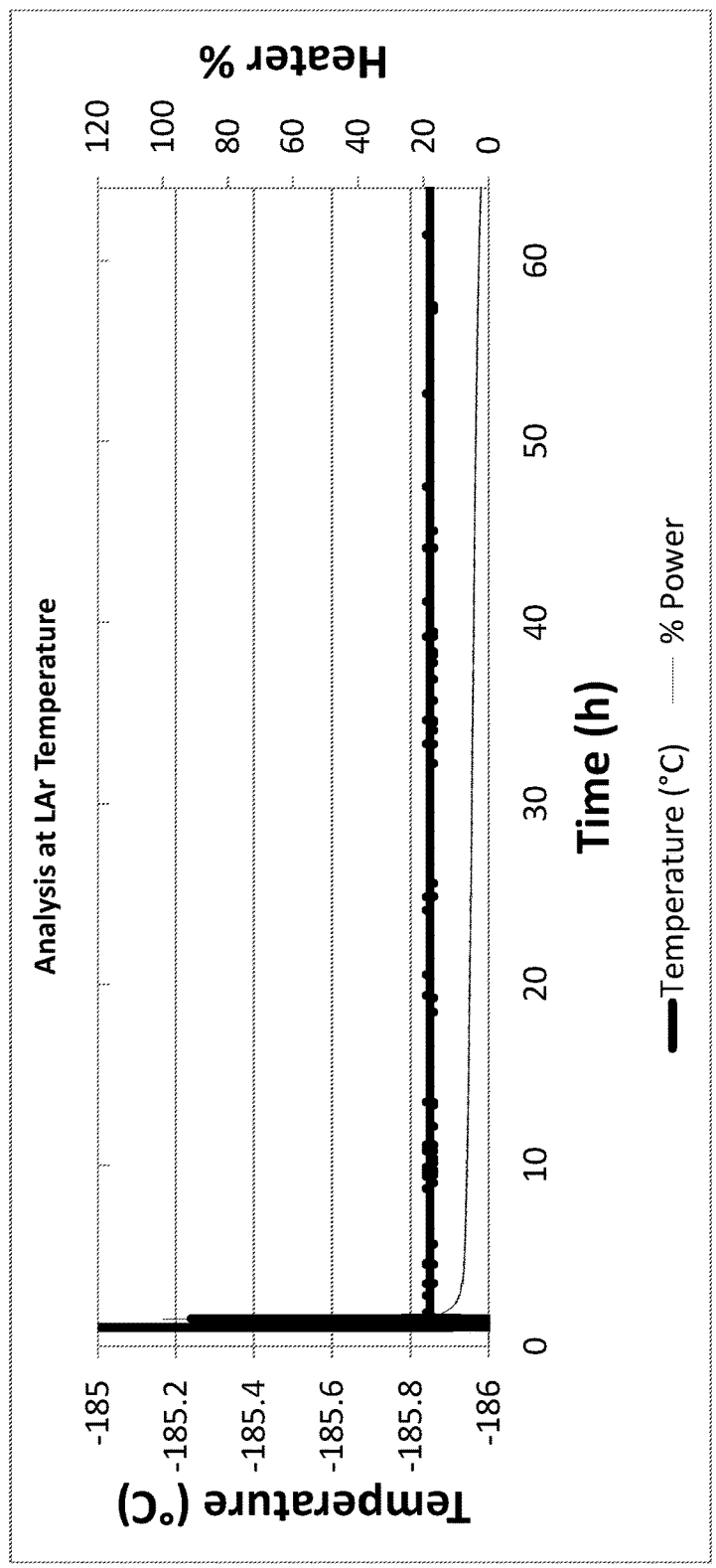
FIG. 4 is a graph representing the temperature maintained by the device over time in hours and the heater power required over time.

When the assembly 20 is in operation, the exposed surface 3e is submerged within liquid Nitrogen, or a similar cryogenic fluid 2, within the basin 1b of the vacuum flask 1 such that the exposed surface 3e of the heat sink 3 is in direct contact with the cryogenic fluid 2. This is done to provide physical stability to the system while also providing an optimal duration contact between the exposed surface 3e of the heat sink 3 and the cryogenic fluid 2. The system described can maintain the target temperature in the thermostatic block for a long period (dependent on specific configuration) as shown in FIG. 4. This allows the analysis duration using the system to be extended indefinitely if the cryogenic fluid is refilled either manually or automatically. Such is made possible by the fact that the refilling process has an insignificant effect on the thermostatic block temperature stability.

Figure 3:
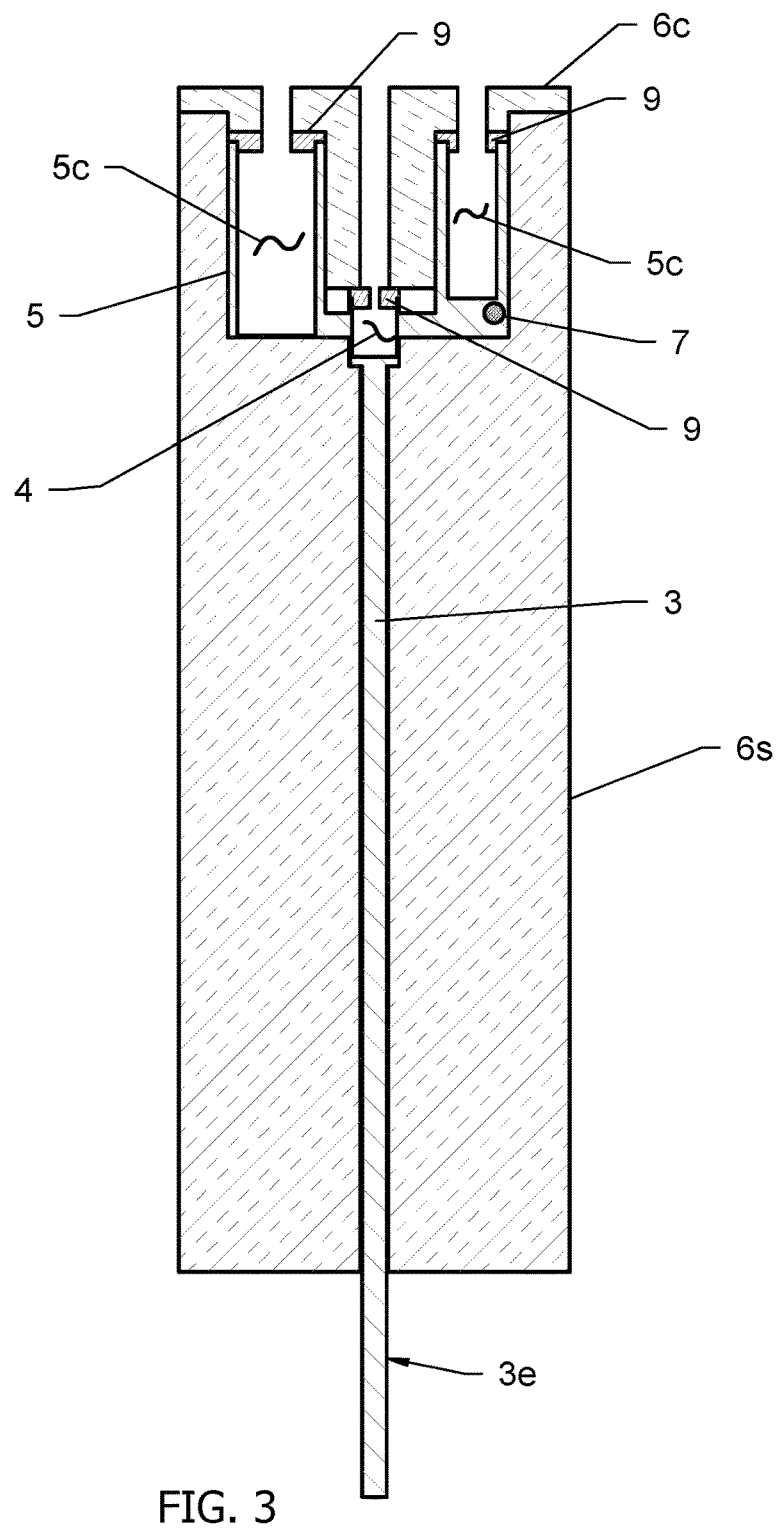
FIG. 3 is a side view of another embodiment of the cryogenic temperature control device.
Figure 3A:
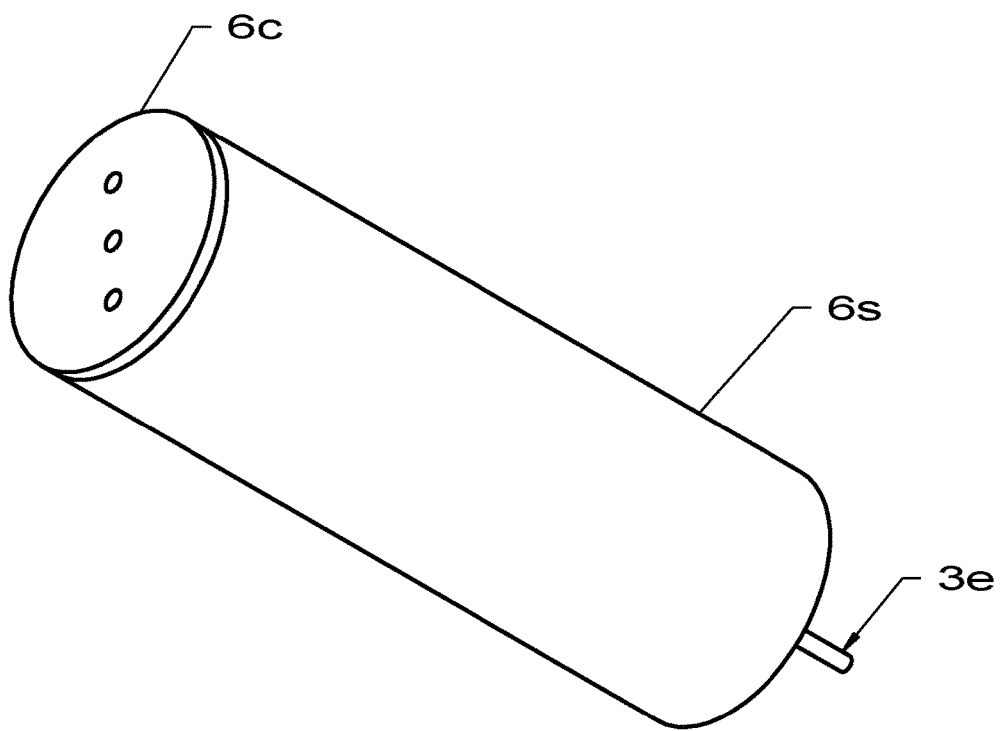
FIG. 3A is a perspective view of the cryogenic temperature control device of FIGS. 3.

FIG. 3 shows an embodiment in which two chambers 5c are provided in a common thermostatic block 5 of thermally conductive material (greater than 35 W/m*K). The figure shows the possibility of two different size chambers 5c being controlled by a common heater 4 and temperature probe 7. Each of the chambers 5c have a respective sample holder (not shown). In a viewing direction toward the figure, it is shown that the left hand chamber 5c is larger in diameter and in length than the right hand side chamber 5c. Accordingly, in order to maintain a common temperature in the thermostatic block 5, the thermostatic block 5 has substantially an identical mass for the left and right side chambers 5c. This can be achieved as shown, by the right side chamber 5c having a greater wall thickness than the left side chamber 5c, along with a thickness at the base of the right side chamber 5c being greater than at the base of the left side chamber 5c.

The heat sink 3 is provided as a rod 3 that is disposed centrally between the two chambers 5c at the base of the thermostatic block 5 and is of thermally conductive material (greater than 35 W/m*K). The rod 3 extends into a basin 1b, as shown above with respect to FIGS. 1 and 2. The rod 3 can be a one-piece construction with the block 5 or can be welded thereto if provided as individual components. In FIG. 3, the insulation cap 6c includes a center portion that extends between the two chambers 5c. The center portion of the insulation cap 6c includes a channel, which serves as a passage for wiring (not shown) to the heater 4 disposed at a recess above the rod 3. The recess is provided with a lid 9 in the similar to the chambers 5c. This embodiment also includes an insulation sleeve 6s that surrounds a portion of the rod 3 and the thermostatic block 5. The rod 3 includes the exposed surface 3e. The heater 4 is provided at the juncture of the heat sink rod 3 and the thermostatic block 5 and provides energy to the thermostatic block 5 under the direction of the controller 12, as discussed with respect to FIGS. 1 and 2. The temperature probe 7 can be provided in or at either of the two chambers 5c. This is possible because, as mentioned above, the thermostatic block 5 has identical mass and material for each of the chambers 5c. Similar to above, it is possible to provide the chambers 5c with respective heat sinks 3 each having respective heaters 4. It is also possible for the chambers 5c to be disposed in respective thermostatic blocks 5. Additionally, any of the other specific features of FIGS. 1 and 2 can be included in the embodiment of FIG. 3.

We claim:

1. A cryogenic temperature controller assembly comprising:
   a controller;
   a thermostatic block having a chamber for receiving a sample holder therein, said thermostatic block having a heat sink with an exposed surface for exposure to a cryogenic fluid;
   a heater disposed intermediate said exposed surface and said chamber, said heater being connected to said controller;
   a temperature probe disposed in said thermostatic block, said probe being connected to said controller, said controller regulating said heater based on an actual temperature from said probe for maintaining a predetermined set point temperature in said thermostatic block.

2. The cryogenic temperature controller assembly according to claim 1, further comprising an insulation sleeve at least partially surrounding said thermostatic block.

3. The cryogenic temperature controller assembly according to claim 2, wherein said insulation sleeve includes a portion surrounding said heat sink.

4. The cryogenic temperature controller assembly according to claim 3, wherein further comprising an insulation cap mating with said insulation sleeve and covering an end of said thermostatic block.

5. The cryogenic temperature controller assembly according to claim 1, wherein said heat sink is a rod that is thermally conductively connected to said thermostatic block and extends therefrom.

6. The cryogenic temperature controller assembly according to claim 5, wherein said heater is disposed at a juncture between said rod and said thermostatic block.

7. The cryogenic temperature controller assembly according to claim 6, further comprising a threaded connection between said thermostatic block and said rod.

8. The cryogenic temperature controller assembly according to claim 7, wherein said threaded connection includes a female tap hole with a base, said heater is disposed in said tap hole at said base.

9. The cryogenic temperature controller assembly according to claim 1, further comprising a vessel having a basin for receiving said thermostatic block and said heat sink and the cryogenic fluid.

10. The cryogenic temperature controller assembly according to claim 9, wherein said heat sink is a rod that is thermally conductively connected at a connection to said thermostatic block, said rod extends to a position next to a base of said basin to allow said exposed surface to maintain contact with the cryogenic fluid at a low level of fill of said basin.

11. The cryogenic temperature controller assembly according to claim 10, wherein said rod has a free end opposite of said connection, said free end having an end cap for preventing said rod from damaging said basin.

12. The cryogenic temperature controller assembly according to claim 1, further comprising a sample holder at least partially disposed in said chamber.

13. The cryogenic temperature controller assembly according to claim 1, further comprising an insulation sleeve at least partially surrounding said thermostatic block and a portion at least partially surrounding said heat sink.

14. The cryogenic temperature controller assembly according to claim 13, further comprising an insulation cap covering an end of said thermostatic block.

15. The cryogenic temperature controller assembly according to claim 1, wherein said thermostatic block has two chambers for simultaneously carrying out two separate sample analyses.

16. A cryogenic temperature controller assembly comprising:
    a thermostatic block having a chamber for receiving a sample holder therein, said thermostatic block having a heat sink with an exposed surface for exposure to a cryogenic fluid;
    a temperature probe disposed in said thermostatic block;
    a heater disposed and configured for maintaining a predetermined set point temperature in said thermostatic block by introducing thermal energy on the basis of actual temperatures observed by said temperature probe.

17. The cryogenic temperature controller assembly according to claim 16, further comprising an insulation sleeve at least partially surrounding said thermostatic block.

18. The cryogenic temperature controller assembly according to claim 16, further comprising a controller connected to said heater and said temperature probe, said controller regulating said heater based the actual temperatures observed by said probe for maintaining the predetermined set point temperature in said thermostatic block.

19. A method for maintaining a predetermined set point temperature during a testing period, the method comprising:
    providing a thermostatic block having a heat sink with an exposed surface;
    bringing the exposed surface of the heat sink into contact with a cryogenic fluid during the testing period for cooling the thermostatic block;
    regulating a heater disposed for maintaining the predetermined set point temperature in the thermostatic block by introducing thermal energy into the thermostatic block on the basis of actual temperatures observed by the temperature probe for maintaining the predetermined set point temperature in the thermostatic block during the testing period.

* * * * *